United States Patent [19]

Riley

[11] Patent Number: 4,610,544
[45] Date of Patent: * Sep. 9, 1986

[54] FLOW ANALYSIS

[76] Inventor: Clifford Riley, Terracotta, Wellhouse Lane, Burgess Hill, Sussex RH15 OBN, United Kingdom

[*] Notice: The portion of the term of this patent subsequent to Dec. 4, 2001 has been disclaimed.

[21] Appl. No.: 615,826

[22] Filed: Jul. 9, 1984

Related U.S. Application Data

[63] Continuation of Ser. No. 300,660, Sep. 9, 1981, Pat. No. 4,486,097.

[51] Int. Cl.$^4$ ............................ G01N 35/08; G01J 3/00
[52] U.S. Cl. ...................................... 356/410; 422/64; 422/82; 436/53
[58] Field of Search .................. 356/410, 411; 422/81, 422/82, 64, 67; 436/52, 53

[56] References Cited

U.S. PATENT DOCUMENTS

| | | |
|---|---|---|
| 3,489,525 | 1/1970 | Natelson . |
| 3,534,379 | 10/1970 | Pelavin . |
| 3,690,833 | 9/1972 | Ferrari . |
| 3,737,251 | 6/1973 | Berman, et al. . |
| 4,022,575 | 5/1977 | Hansen et al. . |
| 4,177,677 | 12/1979 | Ruzicka et al. . |
| 4,486,097 | 12/1984 | Riley .................... 356/410 |

FOREIGN PATENT DOCUMENTS

| | | |
|---|---|---|
| 2408141 | 6/1979 | France . |
| 2446480 | 8/1980 | France . |
| 1098573 | 1/1968 | United Kingdom . |
| 1185917 | 3/1970 | United Kingdom . |
| 1226128 | 3/1971 | United Kingdom . |
| 1432608 | 4/1976 | United Kingdom . |
| 1464235 | 2/1977 | United Kingdom . |
| 1477164 | 6/1977 | United Kingdom . |
| 1475608 | 6/1977 | United Kingdom . |
| 2023286 | 12/1979 | United Kingdom . |
| 1596633 | 8/1981 | United Kingdom ................ 422/64 |

OTHER PUBLICATIONS

Krottinger et al., *American Laboratory*, vol. 9, No. 3, Mar. 1977, pp. 51-59.

Primary Examiner—F. L. Evans

[57] ABSTRACT

A method and apparatus for analysis of liquid samples is described. The method involves simultaneously introducing a predetermined quantity of a given sample and a predetermined quantity of a selected reagent therefor directly into separate flow lines by aspiration from separate containers; bringing the extracted sample and the extracted reagent together into a common flow channel; and causing the sample/reagent mixture to travel along the flow channel as a discrete liquid slug interposed in the stream of a carrier liquid to the measurement cell of an analytical instrument. Another aspect of the method is characterized in that a single pump is used to draw sample and reagent into separate arms of the flow channel which subsequently merge, and to drive the sample/reagent mixture along the flow channel; and in that a carrier liquid is drawn into the flow channel by said pump so that the material within the flow channel is carried along as a continuous liquid phase. The apparatus comprises means for extracting the sample and reagent; a peristaltic pump for driving material along the flow channel; a stepping motor connected or connectable to drive the peristaltic pump, the stepping motor being controllable (preferably by a microprocessor) so that it can make precise angular movements; means, for example a Y-piece or T-piece, for bringing the extracted sample and the extracted reagent together into a common flow channel; and means for deriving an analytical measurement from material in the flow channel. The method and apparatus are particularly well suited for use in the automatic analysis of samples of clinical interest.

2 Claims, 1 Drawing Figure

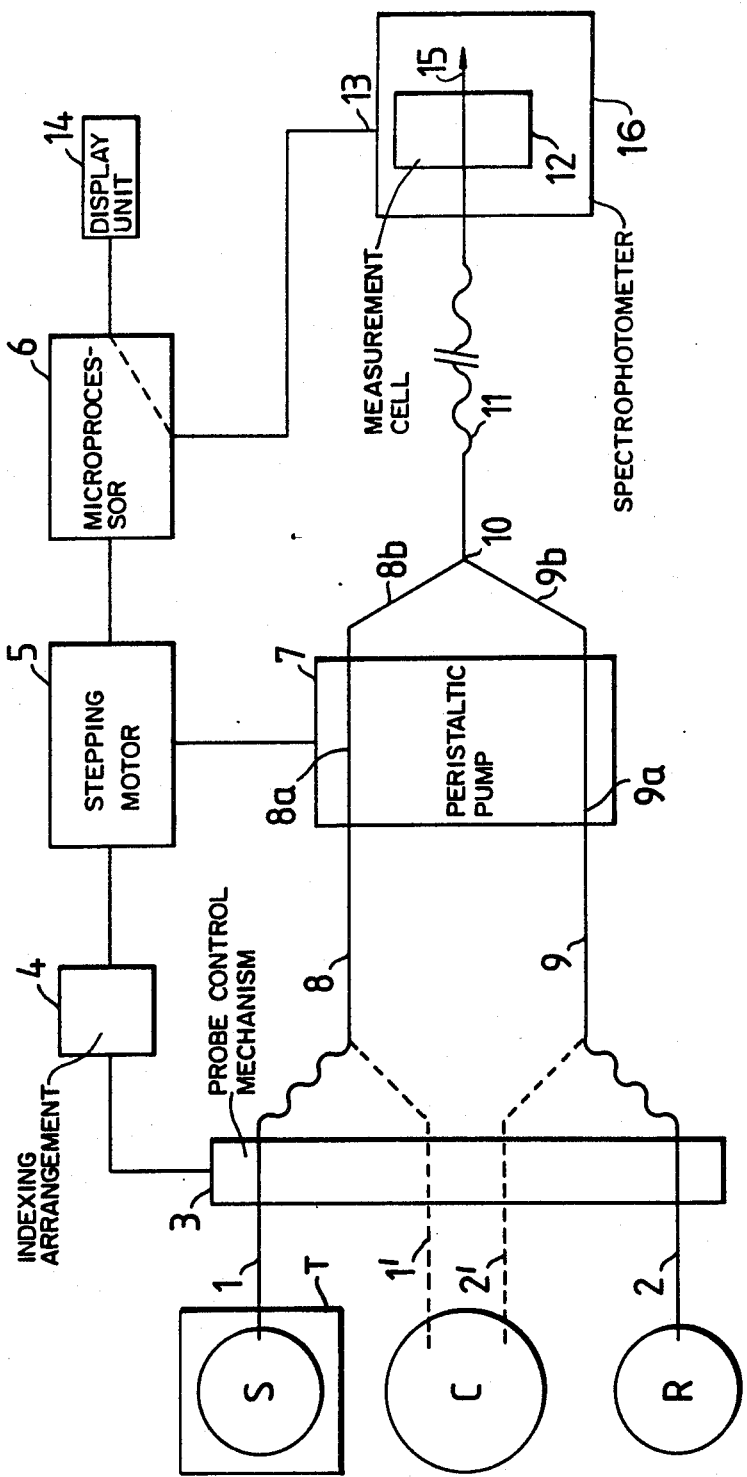

FLOW ANALYSIS

This is a continuation of application Ser. No. 300,660, filed Sept. 9, 1981, now U.S. Pat. No. 4,486,097.

BACKGROUND OF THE INVENTION

This invention relates to the analysis of samples which are caused to flow along a flow channel. The method and apparatus of the invention are particularly well suited for use in the automatic analysis of samples of clinical interest, but are also well suited for use in the automatic analysis of agricultural, pharmaceutical and industrial samples.

Various types of analytical apparatus are known. One type of apparatus is known as a discrete analyser, and in this apparatus a sample is placed in an individual container where, in general, it remains for the duration of the analytical procedure which is carried out. An advantage of this arrangement is that each discrete sample can be individually labelled, so that confusion between different samples is minimised.

A further type of analyser mixes a sample under investigation with a reagent by injecting them into a chamber from which the reacting mixture is passed to a measurement cell. The mixture is held in this cell for a short time while a measurement, for example a photometric measurement, is carried out.

In a further type of apparatus, samples travel continuously in a carrier stream moving along a narrow flow channel which is designed so that each individual sample retains its integrity with respect to adjacent samples. In one system, slugs of air are used to separate individual samples in the moving stream. In another system, known as flow injection analysis, the carrier medium is the reagent with which the individual samples are to react. A precisely measured sample is injected into the flowing reagent stream at a given point. Injection can take place with a syringe, e.g. through a septum or by means of a rotary valve. In the latter case, the port in the rotary valve constitutes the measuring device; a slight excess of sample is injected through the port which is then rotated to deliver its contents into the flowing reagent stream. The injected slug of sample remains coherent as it passes along the narrow tubing which constitutes the flow channel, although the sample becomes elongated. The sample mixes with reagent by radial diffusion from the boundary layer. Successful operation of this flow injection analysis technique therefore requires that turbulent flow is avoided. This arrangement offers advantages over the system using air-segmented samples, in that it allows more rapid sampling rates without adverse effects on the accuracy of the analytical results obtained. The system does, however, have the disadvantage that it is wasteful of reagent, which in many cases will be an expensive commodity.

SUMMARY OF THE INVENTION

According to one aspect of the present invention, there is provided a method of analysis of a liquid sample which is carried along a flow channel to the measurement cell of an analytical instrument, which is characterised in that a single pump is used to draw sample and reagent into separate arms of the flow channel which subsequently merge, and to drive the sample/reagent mixture along the flow channel; and in that a carrier liquid is drawn into the flow channel by the said pump so that the material within the flow channel is carried along as a continuous liquid phase.

According to a second aspect of the present invention, there is provided a method of analysis of a liquid sample which is carried along a flow channel by a carrier liquid, which method comprises simultaneously introducing a predetermined quantity of a given sample and a predetermined quantity of a selected reagent directly into separate flow lines by aspiration from separate containers; bringing the extracted sammple and the extracted reagent together into a common flow channel; and causing the sample/reagent mixture to travel along said flow channel as a discrete liquid slug interposed in a stream of carrier liquid to the measurement cell of an analytical instrument.

In contrast to known techniques, the method of this invention involves aspiration of sample and reagent into separate flow lines which subsequently merge or join, rather than using the injection of sample and reagent (whether separately or together) into a carrier liquid already present in a flow channel. Thus the method of the invention does not require there to be any liquid in the flow lines at the time that the sample and reagent are introduced.

The method of the invention can be used in the sequential analysis of a series of samples. It can operate with a plurality of samples simultaneously present at different positions within the flow channel, or with just a single sample at any one time within the flow channel.

The method of this invention does not require the use of air bubbles to segment the carrier liquid. Thus the material present in the flow channel is in the form of a continuous liquid, the carrier liquid having interposed therein discrete liquid slugs of sample/reagent mixture (hereinafter called "active slugs"). Conveniently, the carrier liquid is distilled water; there is no need to use a carrier liquid which is immiscible with the active slug.

The method operates under conditions of laminar flow in the flow channel, and only relatively low pressures are required to pump the material along the flow channel.

The flow channel is preferably constituted by clear piping of internal diameter not greater than 1 mm; commercially available polyethylene or polypropylene tubing has proved to be satisfactory.

Preferably, the sample and reagent are extracted from their respective containers by probes or dip-tubes which are connected to narrow bore tubing which leads to a peristaltic pump. The probes can remain in a source of carrier liquid until an active slug is to be introduced into the flow channel. The probes are then transferred from the source of carrier liquid to the respective containers of sample and reagent.

The peristaltic pump is preferably driven by a stepping motor under control of a microprocessor so that the motor can make precisely controlled angular movements. This in turn effects precise control on the proportions of active slugs and carrier liquid which pass along the flow channel. As well as allowing precise control of the material in the flow channel, the use of a stepping motor controlled by a microprocessor enables the method of the invention to be very flexible, in that the size of successive samples, the gap between successive samples and the time selected for the analytical measurement of samples can all be varied independently.

It is preferred that the quantity of reagent extracted should exceed that of sample; thus when the sample and reagent are brought together, which is preferably at a Y-piece or T-piece made for example, of plastics tubing, the active slug thereby formed ensures excellent mixing of sample with reagent while being very economical in terms of the quantity of reagent which is used.

The pump tube provided for that probe which, in use, extracts reagent can be of a larger diameter than the other pump tube. Thus a given angular rotation of the peristaltic pump will cause the quantity of reagent which is taken up to be larger than that of the sample which is to be investigated.

Generally, the flow channel will include a coil of narrow bore tubing of a length sufficient to give the desired contact time between sample and reagent. The flow channel would also include an analytical station, for example the flow cell of a colorimeter.

According to another aspect of the present invention, there is provided apparatus for the analysis of liquid samples carried along a flow channel by a carrier liquid, which apparatus comprises means for simultaneously introducing predetermined quantities of a given sample and of a selected reagent directly into separate flow lines by aspiration from separate containers; a peristaltic pump for pumping liquid along the flow channel; a stepping motor connected or connectable to drive the peristaltic pump, the stepping motor being controllable so that it can make precise angular movements; means for bringing the extracted sample and the extracted reagent together into a common flow channel; and means for deriving an analytical measurement from material in the flow channel.

The means for deriving an analytical measurement can be, for example, a spectrophotometer.

Advantageously, the stepping motor is controlled by a microprocessor. The same microprocessor may also be used to control the analytical instrument, e.g. a spectrophotometer, and to process data produced by that instrument.

The apparatus may also include a turntable for receiving and holding samples which are to undergo analysis; the turntable is preferably controlled by an indexing arrangement actuated directly or indirectly by the stepping motor and controlled by the microprocessor.

The method and apparatus of the invention are especially useful in clinical analysis. The method and apparatus may be used to obtain data from instantaneous reactions between sample and reagent; for example, in the measurement of serum calcium levels, the sample is mixed with a reagent consisting of a solution of cresolphthalein complexone. A blue colour develops immediately the intensity of which is proportional to the concentration of calcium in the sample. With an instantaneous reaction of this sort, the active slug can be pumped through the flow cell of a colorimeter without stopping, and the maximum signal derived from the photometer represents the calcium concentration of the sample in question.

The method and apparatus may also be used to derive data from samples which undergo a slow reaction with their reagent. Thus in the measurement of serum glucose levels, a sample of the serum under investigation is mixed with the enzyme glucose dehydrogenase. The mixture is incubated, typically at 30° C., and as a result of the reaction the coenzyme nicotinimide adenine dinucleotide is converted into its reduced form which absorbs light in the ultraviolet region of the spectrum. In investigations of this type, the active slug is pumped into the flow cell of the colorimeter; the pump is then stopped and the signal from the colorimeter is observed for a predetermined period, for example 15 seconds. The rate of change of the colorimeter signal in the course of the observation is then proportional to the concentration of glucose in the serum sample.

BRIEF DESCRIPTION OF THE DRAWING

One embodiment of the apparatus of the invention will now be described, by way of example, with reference to the accompanying drawing which illustrates the apparatus diagrammatically.

The drawing shows a pair of probes 1 and 2 inserted into, respectively, a container S containing a sample which is to be analysed, and a container R which contains a reagent which is to be reacted with the sample S. A probe control mechanism 3 is provided which is operated by a stepping motor 5 through an indexing arrangement 4. The probe control mechanism serves to transfer the probe from sample and reagent containers to a third container C which is a source of inert carrier liquid, for example distilled water. The alternative positioning of the probes in container C is indicated by the dashed lines 1' and 2'. The sample container S is located on a turntable (shown diagrammatically at T) which carries a series of samples which are to be analysed sequentially by the apparatus and which is driven by the indexing arrangement 4. The stepping motor 5 is controlled by a microprocessor 6. The apparatus also includes a peristaltic pump 7 the operation of which is effected by stepping motor 5 under control of microprocessor 6. Material within probes 1 and 2 is drawn by the action of peristaltic pump 7 along conduits 8 and 9, respectively (formed by narrow bore plastics tubing) whence they pass through the pump at 8a and 9a, respectively and reach a Y-piece 10, where the two flow streams are combined, via tube portions 8b and 9b, respectively. Downstream of Y-piece 10 there is an elongate channel 11 which leads to the measurement cell 12 of a spectrophotometer 16. The output 13 from the spectrophotometer 16 is fed to microprocessor 6, and one or more analytical parameters derived from output 13 are displayed on a display unit 14. After passing through the measurement cell 12 of the spectrophotometer 16, the fluid is passed to waste at 15. The flow channel through the apparatus consists of probes 1 and 2, conduits 8 and 8a, 9 and 9a, 8b and 9b, Y-piece 10, elongate channel 11 and the passage to disposal at 15. Throughout its length, the flow channel can be formed of narrow bore polyethylene tubing. The internal diameter of the tubing is preferably less than 1 mm. The parts 8a and 9a are generally known as pump tubes; since the action of peristaltic pump 7 is such that its rollers exert a uniform linear driving action over the two pump tubes, the volume of liquid delivered by a given sweep of the pump rollers is proportional to the internal diameter(s) of the pump tubes. Thus by employing tubes 8a and 9a of different internal diameter, the sample: reagent ratio drawn from containers S and R, respectively, can be varied at will.

The apparatus illustrated diagrammatically in the drawing is operated as follows: at the start of an analysis, the two probes are in the position shown by dashed lines 1' and 2', i.e. they both dip into a source of carrier liquid, e.g. distilled water. Operation of peristaltic pump 7 under these conditions will draw distilled water through the apparatus, this serving as a washing function. Operation of the peristaltic pump 7 is stopped, so that there is no fluid flow through the flow channel of the apparatus. Probe control mechanism 3 is then actuated by stepping motor 5 and indexing arrangement 4 to lift the probes from container C and to insert probe 1 into the sample S, and probe 2 into the reagent R. Microprocessor 6 then actuates stepping motor 5 to operate peristaltic pump 7. The pump makes a predetermined angular movement, thus drawing up a precise volume of sample (e.g. serum) and a precise volume of reagent into the probes 1 and 2 respectively. The pump tube 9a is of a larger internal diameter than the pump tube 8a; this serves to ensure that the volume of reagent drawn up by a given angular movement of the pump 7 is larger than the volume of sample drawn up by the same angular movement of the pump. Operation of the peristaltic pump is then stopped, and probe control mechanism 3 transfers the probes 1 and 2 back to the source of carrier liquid C. Peristaltic pump 7 is then actuated once again, so that the sample and reagent already contained within probes 1 and 2 are drawn through the pump 7, while distilled water from container C is drawn through the flow channel immediately behind the sample and reagent so that the material in the flow channel is a continuous liquid phase. Continued operation of the pump causes the respective slugs of sample and reagent to come together at the Y-piece 10, where they merge into a single, active slug which travels along the remainder of the flow channel through the apparatus. Obviously, the path lengths and internal diameters of the tube sections 8b and 9b are arranged to ensure that the sample and reagent reach the Y-piece 10 simultaneously. Meanwhile, the turntable holding samples S is rotated so that the next sample to be analysed is in a position to receive the probe 1. After a predetermined time, operation of the peristaltic pump 7 is stopped once more, so that flow of material through the flow channel of the apparatus comes to a halt. Probe control mechanism 3 then transfers the probes to the containers S and R so that the next sample to be analysed can be drawn into the apparatus together with the reagent therefor.

It will be seen that continued operation in the manner described above results in a series of active slugs passing through the flow channel of the apparatus. Depending on the selected mode of operation, there may be a plurality of active slugs present simultaneously in the flow channel each separated by a predetermined column of carrier liquid, e.g. distilled water; alternatively, the apparatus can be controlled so that a new sample is introduced into the flow channel only when the previous sample has passed through the flow channel and has gone to waste.

Each active slug can comprise terminal regions composed almost entirely of pure reagent, with a central region between them in which sample and reagent are intimately mixed. As each active slug passes along the elongate channel 11, reaction between sample and reagent takes place. The elongate channel 11 will be of a length sufficient to ensure complete mixing between sample and reagent. As the active slug reaches the measurement cell 12 of the spectrophotometer 16, an optical measurement is taken which is fed as output 13 to the microprocessor 6. The output may be displayed directly on display unit 14, or the microprocessor may be used to calculate one or more analytical parameters derived from the optical measurement.

The nature of the sample and that of the reagent involved in any particular analysis will determine which of these two arrangements is adopted.

Similarly, the optical measurement taken by the spectrophotometer may take place with the active slug flowing continuously through the spectrophotometer, or it may take place with the active slug held stationary within measuring cell 12. The first course will be adopted where the reaction between sample and reagent is instantaneous, or where it is complete by the time the active slug reaches the measurement cell 12, and the second course will be adopted where the reaction between sample and reagent is a slow reaction, i.e. one which is still proceeding at the time the active slug reaches measurement cell 12.

The apparatus described above operates at relatively low pressures and under conditions of laminar flow. The material within the flow channel is a continuous liquid—no segmentation by air bubbles or immiscible liquids is necessary in order to preserve the integrity of adjacent active slugs. A high throughput of samples is possible, and furthermore the sampling rate can be varied according to the nature of sample and reagent which are undergoing analysis. The use of microprocessor 6 to operate stepping motor 5 enables great accuracy to be obtained in the volumes of samples and reagent which are drawn up into the apparatus. The volume ratio between sample and reagent is determined by the ratio between the internal diameters of pump tubes 8a and 9a which are in the form of plastics tubing. It is a relatively simple matter to change one or both of the pump tubes in order to alter the desired volume ratio and hence to alter the relative proportions of sample and reagent which are drawn through the apparatus. The microprocessor 6 can be programmed to act on stepping motor 5 so as to adjust the sampling size, the length of the column of carrier liquid provided between adjacent samples, and the hold time of material within measuring cell 12.

The invention will be further illustrated by the following Examples.

EXAMPLE 1

The apparatus of the invention was used to perform an assay of serum creatinine by the kinetic Jaffé method. This uses the red coloration formed when creatinine reacts with picric acid (2,4,6-trinitrohenol) and sodium hydroxide to estimate the quantity of creatinine present in the sample. A spectrophotometer having a 7-volt lamp as the light source and a 505 nm filter was used to detect the development of the coloration. The pump tube 8a (for the serum sample under investigation) had an internal diameter of 0.03 inches (0.76 mm) while the pump tube 9a (for the picric acid/sodium hydroxide reagent) had an internal diameter of 0.065 inches (1.65 mm). The flow channel 11 consisted of a coiled plastics tube of internal diameter of 0.03 inches (0.76 mm) wound about a thermostatically controlled heater arranged to maintain the liquid within the flow channel at a uniform 25° C. The peristaltic pump 7, when driven, was operated at 75 revolutions per minute. The microprocessor was programmed to operate the pump with a 10 second aspiration period in which sample and reagent were drawn directly into their separate flow lines 1 and 2, respectively, after which the pump was stopped while the probes were transferred to container C which held deionised water as the carrier liquid. The size of the pump tubes together with the 10 second aspiration resulted in the extraction of 15 microliters of sample from container S and 65 microliters of reagent from container R. The pump was then operated for a further 3 seconds, which effected the transport of the active slug formed at 10 to the measurement cell 12 of the spectrophotometer. The pump was then halted for a period of 15 seconds, during which the colour change within cell 12 was monitored. The active slug was then flushed out of the flow line by a further operation of the pump 7 for a period of 6 seconds. Thus the cycle time per sample was 34 seconds. The determination of the creatinine level of the sample was effected by standard colorimetric analysis and the result was obtained at 14.

EXAMPLE 2

In order to assess the accuracy of the apparatus and method as described in Example 1, the analytical run was repeated with 20 serum samples and the results were recorded. The same samples were then analysed by the same kinetic Jaffé method on a commercially available centrifugal analyser (a Centrifichem 400 analyser manufactured by Union Carbide Limited) and the results were compared. The two sets of results were to all intents and purposes identical, the correlation coefficient (r) being r=0.98.

EXAMPLE 3

The precision of the method as described in Example 1 was assessed by using pre-prepared creatinine solutions as samples. Ten analytical runs were completed with creatinine levels at (a) 128 millimols/liter, (b) 330 millimols/liter and (c) 970 millimols/liter. The coefficient of variation (cV) was calculated for each of the three levels: cV is the standard deviation expressed as a percentage of the mean value, and is also known as relative standard deviation. The results obtained were as follows:

| Creatinine level (mmol/l) | cV (%) |
| --- | --- |
| 128 | 6.0 |
| 330 | 2.6 |
| 970 | 3.5 |

While the apparatus has been described in relation to the measurement of an optical parameter using a spectrophotometer, other analytical instruments may be used as well as, or instead of, a spectrophotometer, depending upon the nature of material being investigated. Thus it may be valuable, in some analyses, to make electrochemical measurements on the material passing through the flow channel, for example by means of a polarograph.

What is claimed is:

1. A method of analysis of a liquid sample which is carried along a flow channel by a carrier liquid, which method comprises introducing a predetermined quantity of a given sample and a predetermined quantity of a selected reagent into respective separate sample and reagent flow lines by aspiration from separator containers, the sample being aspirated by a movable hollow probe, bringing the extracted sample and the extracted reagent together into a common flow channel, and causing the combined sample and reagent to travel along said flow channel to a measurement cell, the sample and reagent being caused to flow along the flow channel by a pump, and after the predetermined quanitities of sample and reagent have been aspirated, (a) transferring the hollow probe while pump action is momentarily stopped to receive flow of a carrier liquid whereafter the pump is re-started and (b) transferring the reagent flow line during the time the pump action is momentarily stopped to receive flow of a carrier liquid, whereby the sample and reagent are caused to travel along said flow channel as a discrete liquid slug interposed in a stream of carrier liquid.

2. Apparatus for the analysis of liquid samples carried along a flow channel by a carrier liquid, said apparatus comprising a first container for the material a sample of which is to be analyzed; a second container for a reagent to be admixed with said sample; a third container for a carrier liquid; a first hollow probe for insertion into either said first container or said third container; a probe control mechanism for controlling placement of said first hollow probe alternatively in the first and third containers; a first conduit communicating with said first hollow probe; a second conduit; a common flow channel at one end of which said first and second conduits come into confluence; a pump for pumping liquids along said first and second conduits and said common flow channel; means for deriving an analytical measurement from material in said common flow channel; drive means for driving the pump; means for alternatively connecting the second conduit with the second and third containers, whereby the sample and reagent can be caused to travel along said flow channel as a discrete slug interposed in a stream of carrier liquid.

* * * * *